(12) United States Patent
Ding et al.

(10) Patent No.: US 8,394,999 B2
(45) Date of Patent: Mar. 12, 2013

(54) PROCESS FOR CONVERTING GLYCERIN INTO PROPYLENE GLYCOL

(75) Inventors: Zhongyi Ding, Katy, TX (US); Joseph Chiu, Katy, TX (US); Weihua Jin, Katy, TX (US)

(73) Assignee: GTC Technology US LLC, Houston, TX (US)

( * ) Notice: Subject to any disclaimer, the term of this patent is extended or adjusted under 35 U.S.C. 154(b) by 0 days.

(21) Appl. No.: 13/417,696

(22) Filed: Mar. 12, 2012

(65) Prior Publication Data

US 2012/0232312 A1 Sep. 13, 2012

Related U.S. Application Data

(60) Provisional application No. 61/451,246, filed on Mar. 10, 2011.

(51) Int. Cl.
*C07C 29/132* (2006.01)
(52) U.S. Cl. .................................................. 568/861
(58) Field of Classification Search ................... 568/861
See application file for complete search history.

(56) References Cited

U.S. PATENT DOCUMENTS 7,586,016 B2 * 9/2009 Cui et al. ...................... 568/861
7,619,118 B2 * 11/2009 Arredondo et al. ........... 564/471

* cited by examiner

*Primary Examiner* — Elvis O Price
(74) *Attorney, Agent, or Firm* — Winstead PC

(57) ABSTRACT

A process to convert glycerin into propylene glycol and purifying the produced propylene glycol is described. The glycerin-based propylene glycol production requires only one process step compared to petroleum/natural gas-based propylene glycol production requires multiple process steps, and thus represents a cost savings.

11 Claims, 1 Drawing Sheet

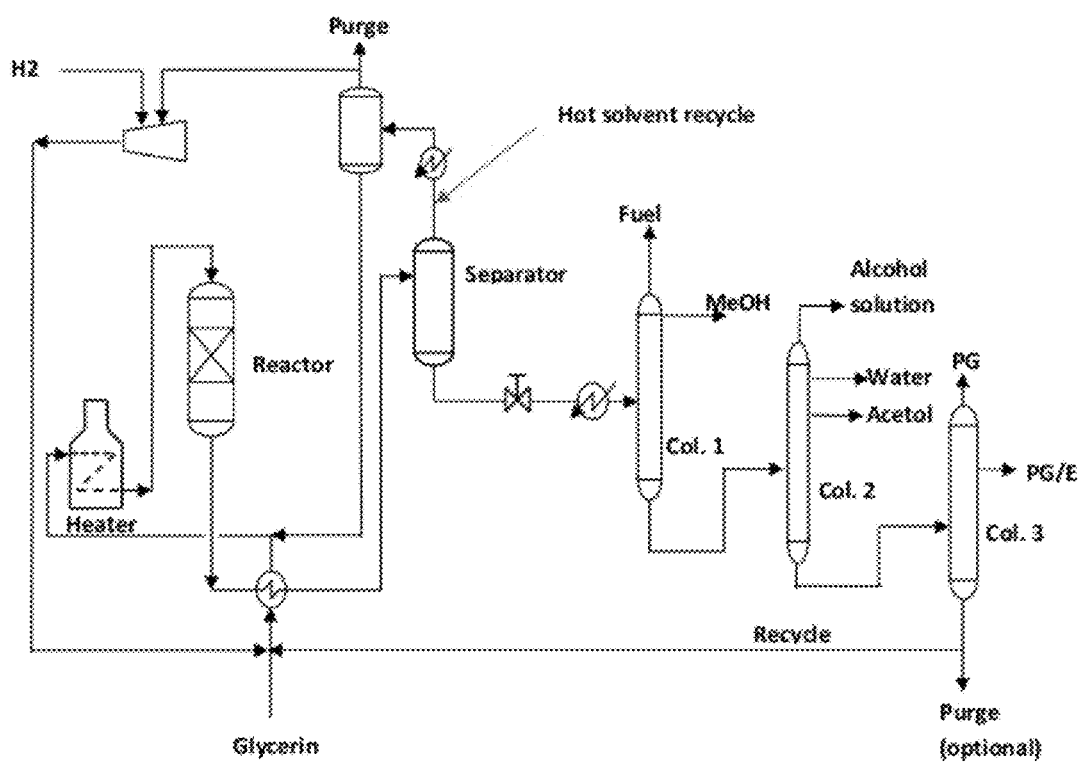

PROCESS FOR CONVERTING GLYCERIN INTO PROPYLENE GLYCOL

CROSS-REFERENCES TO RELATED APPLICATIONS

This Application claims the benefit under 35 U.S.C. 119(e) of U.S. Provisional Patent Application Ser. No. 61/451,246 filed Mar. 10, 2011, which is incorporated herein by reference in its entirety as if fully set forth herein.

FIELD OF THE INVENTION

This invention relates to a process for converting glycerin to propylene glycol and purifying the propylene glycol that is produced.

BACKGROUND OF THE INVENTION

The world is collectively engaged in a massive search for energy alternatives to ever higher priced crude oil. Among these alternatives, biodiesel has gained importance in recent years for its ability to mix with petroleum diesel. Biodiesel refers to a diesel-equivalent fuel consisting of short chain alkyl (methyl or ethyl) esters, made by transesterification of triglycerides, commonly known as vegetable oils or animal fats. The most common form uses methanol, the cheapest alcohol available, to produce methyl esters. The molecules in biodiesel are primarily fatty acid methyl ester (FAME), usually created by transesterification between fats and methanol. Currently, biodiesel is produced from various vegetable and plant oils.

One by-product of the transesterification process is glycerin (glycerol). For every 1 ton of biodiesel manufactured, 100 kg of glycerin is produced. Historically, there was a valuable market for the glycerin, which assisted the economics of the overall biodiesel process. With the increase in global biodiesel production, however, the by-product glycerin has saturated the market, which in turn has caused the market price of the crude glycerin to fall. The valuable disposition of this crude glycerin is vitally important to making the renewable biodiesel process more efficient in carbon utilization while offsetting production costs.

Glycerin usage is primarily used in foods and beverages, pharmaceutical and personal care, and fine chemicals. Glycerin is an oxygenated three carbon chemical. With the rapid expansion of biodiesel production, glycerin has become an abundant and inexpensive raw material. This character brings glycerin in as a potential chemical building block for other important renewable/green chemicals.

Two main classes of petrochemical raw materials are olefins (including ethylene and propylene) and aromatics (including benzene and xylene isomers), both of which are produced in very large quantities. They are the building blocks of chemicals and plastics we are using daily. These petroleum based commodity chemicals are not immune to resource limitation and increasing cost that we face in the fuel industry today. The search of alternative sources is vital important. The strategic development for technologies in bio-chemicals and process integration with biofuels could be similar to the current petroleum-based processes. The building block chemicals must be relatively easy and cheap to produce in large quantities. They should have chemical structures that facilitate their conversion into multiple products of commercial interest. Therefore, both bioethanol and glycerin have potential to be the building block chemicals for petroleum-based ethylene and propylene derivatives. The modernized biodiesel production enables the production of glycerin in large quantities at very low costs, which qualifies it for future development as one of the building block chemicals.

Propylene glycol is the preferred choice due to its established market and large consumption. One particularly interesting propylene glycol substitution is its use as a "green" non-toxic antifreeze and de-icing fluid. Propylene glycol is currently produced from petrochemical derived propylene. It has broad established market applications and potential for other applications. The successful conversion of glycerin to propylene glycol and the utilization of glycerin as a potential petrochemical feedstock shall positively impact the biodiesel business through better carbon utilization, by-product upgrade to high value products, opportunity to develop renewable chemicals, and maximum return on investment.

SUMMARY OF THE INVENTION

An aspect of the invention is directed to a process for converting glycerin into propylene glycol comprising the steps of: preheating a feed mixture comprising glycerin, hydrogen and methanol in a reactant heater; passing the heated feed mixture to a reactor; separating the reactor effluent into a vapor phase stream and a liquid phase stream; condensing the vapor phase stream into a condensed liquid; recycling the condensed liquid to the reactor; and distilling the liquid phase stream to obtain purified propylene glycol.

The cost advantage for this glycerin based propylene glycol process over petroleum-based propylene glycol production stems from its simplicity. The glycerin-based propylene glycol production requires only one process step whereas petroleum/natural gas-based propylene glycol production requires multiple process steps.

BRIEF DESCRIPTION OF THE DRAWINGS

FIG. 1 shows a process scheme for the conversion of glycerin into propylene glycol in accordance with an embodiment of the invention.

DESCRIPTION OF EXEMPLARY EMBODIMENTS

A hydrogenation process is used to convert glycerin into propylene glycol (PG). The process has greater than 95% selectivity to PG and produces 98% or higher purity PG for industrial applications. An exemplary process scheme is shown in FIG. 1.

An embodiment of the invention is directed to a process for converting glycerin into propylene glycol comprising the steps of: preheating a feed mixture comprising glycerin, hydrogen and methanol in a reactant heater; passing the heated feed mixture to a reactor; separating the reactor effluent into a vapor phase stream and a liquid phase stream; condensing the vapor phase stream into a condensed liquid; recycling the condensed liquid to the reactor; and distilling the liquid phase stream to obtain purified propylene glycol.

The claimed invention is directed to a process for converting glycerin to propylene glycol. The process scheme comprises a reaction section to convert glycerin to propylene glycol and a fractionation section to obtain on-spec propylene glycol product. A proprietary catalyst is used comprising a metal or metal oxide dispersed on inert support. The hydrogenation reaction of glycerin is carried out at a temperature of approximately 190° C. and a pressure of 2.0-8.0 MPa (20-80 atmospheres). One-pass glycerin conversion is greater than 70% and propylene glycol selectivity is greater than 95%. The propylene glycol is further purified in the fractionation section to meet various product specifications.

An embodiment of the invention is directed to a process for the conversion of glycerin to propylene glycol by hydrogenation in a fixed bed reactor at a temperature of 150° C.-240° C. and a pressure of 20-80 atmospheres. In certain embodiments of the invention, the reaction temperature is approximately 190° C. In other embodiments of the invention, the operating pressure of the reactor is 20-60 atmospheres.

In some embodiments of the invention, the hydrogenation of glycerin to propylene glycol is performed by a supported catalyst in a fixed bed reactor. In certain embodiments the supported catalyst is a metal or metal oxide catalyst. In some embodiments the metal or metal oxide catalyst comprises a noble metal, transition metal, or a combination of transition metals. In certain embodiments of the invention, the supported catalyst comprises copper.

As set forth in FIG. 1, in an embodiment of the inventive process, a glycerin feed, along with hydrogen and methanol, is preheated in a feed-effluent heat exchanger and reactant heater. The mixture then enters the reactor where the hydrogenation of glycerin to PG takes place. The reactor effluent, passes through a feed-effluent heat exchanger, and enters a high pressure separator, where hydrogen and methanol are separated from PG and glycerin liquid stream. The vapor phase is cooled and the condensed solvent and boosted hydrogen are recycled to the reactor.

In an embodiment of the invention, the liquid stream from the high pressure separator is cooled down and de-pressurized before entering distillation section. In other embodiments of the invention, the liquid stream is depressurized and then cooled down. In an embodiment of the invention, the reactor effluent is passed through three distillation columns, column 1, column 2 and column 3, to separate the reactor effluent into the following streams: fuel gas, methanol, mixed alcohols, process water, acetol mixture (for recycle or product), 99.5% PG, PG/EG mixture, and recycle glycerin. A first distillation column is used in certain embodiments to separate fuel gas and methanol from the reactor effluent. The effluent from the first distillation column is passed into a second distillation column. The second distillation column is used to separate alcohols, water and acetol mixture from the reactor effluent. The effluent from the second distillation column is passed to a third distillation column. The third distillation column is used to separate PG, PG/ethylene glycol (EG) mixture and recycle glycerin from the reactor effluent.

In an embodiment of the invention, a hydrogenation process for converting glycerin into propylene glycol comprises a fixed bed reactor loaded with a supported metal or metal oxide catalyst, where the majority of glycerin in the feed is converted into propylene glycol. The reactor effluent passes into a feed-effluent heat exchanger, and the vapor phase stream is separated from the liquid phase stream. The vapor phase is further condensed and the condensed liquid is recycled to the fixed bed reactor. The liquid phase is further separated by distillation to obtain purified propylene glycol.

In an embodiment of the invention, the fixed bed reactor can be one fixed reactor, two fixed reactors in series, or multi-fixed bed reactors in series.

In another embodiment of the invention, the fixed bed reactor is operated at temperature of 150° C.-240° C., and pressure of 20-60 atmospheres.

In other embodiments of the invention the supported metal or metal oxide catalyst that is used in the inventive process is selected from noble metal, transition metal, or a combination of transition metals. In other embodiments of the invention, the supported catalyst comprises copper.

In an embodiment of the invention, the vapor phase stream is separated from the liquid phase stream using a high pressure gas-liquid separator. In other embodiments of the invention, the vapor phase stream is separated from the liquid phase stream using a column with liquid wash.

In an embodiment of the invention, the vapor phase stream contains recycle solvent such as water, methanol, or other low boiling point chemicals. In another embodiment of the invention, the recycle solvent is a mixture of water and methanol. In a further embodiment of the invention, the recycle solvent is mixed with a glycerin feed and passed into the fixed bed reactor.

In an embodiment of the invention, a portion of the recycle solvent and glycerin mixture is injected between two fixed bed reactors connected in a series.

In an embodiment of the invention, the liquid phase stream is depressurized and then cooled before entering a distillation column. In other embodiments of the invention, the liquid phase stream is first cooled and then depressurized before entering a distillation column.

In certain embodiments of the invention, multiple distillation columns are used in the purification of propylene glycol. These distillation columns can be selected from single shell column, column with side draw, or divided-wall column.

In certain embodiments of the invention, a first distillation column is used in certain embodiments to separate fuel gas and methanol from the reactor effluent. The effluent from the first distillation column is passed into a second distillation column. The second distillation column is used to separate alcohols, water and acetol mixture from the reactor effluent. The effluent from the second distillation column is passed to a third distillation column. The third distillation column is used to separate PG, PG/ethylene glycol (EG) mixture and recycle glycerin from the reactor effluent.

In an embodiment of the invention, the by-products of the process are separated by distillation. In certain embodiments, by-products are mixed alcohols, water, ethylene glycol, acetol, and other trace compounds. In certain embodiments of the invention, the by-product ethylene glycol is a mixture of propylene glycol and ethylene glycol, or high purity ethylene glycol. In other embodiments of the invention, the by-product mixed alcohols contain water. In certain embodiments of the invention, by-products methanol, water, acetol, and ethylene glycol are obtained from side-draw at different distillation columns.

The claimed invention possesses several advantages over prior art processes including:

1. Lower capital cost production compared to conventional PG from Propylene oxide (PO) route;
2. Energy integration options to further reduce operating costs;
3. One-step reaction from glycerin to PG with higher selectivity;
4. Attractive, competitive technology;
5. Technology platform in renewable resources; other technologies could be built along the claimed process;
6. Integrated with biodiesel process for best utilization of carbon resources; and
7. Green chemical as feedstock glycerin is from bio-renewable source.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term comprising does not exclude the presence of other elements or steps.

Furthermore, although individually listed, a plurality of means, elements or method steps may be implemented by e.g. a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category but rather indicates that the feature is equally applicable to other claim categories as appropriate. Furthermore, the order of features in the claims do not imply any specific order in which the features must be worked and in particular the order of individual steps in a method claim does not imply that the steps must be performed in this order. Rather, the steps may be performed in any suitable order. In addition, singular references do not exclude a plurality. Thus references to "a", "an", "first", "second" etc do not preclude a plurality.

The invention claimed is:

1. A process for converting glycerin into propylene glycol comprising the steps of:
   preheating a feed mixture comprising glycerin, hydrogen and methanol in a reactant heater;
   passing the heated feed mixture to a reactor;
   separating the reactor effluent into a vapor phase stream and a liquid phase stream;
   condensing the vapor phase stream into a condensed liquid;
   recycling the condensed liquid to the reactor; and
   distilling the liquid phase stream to obtain purified propylene glycol.

2. The process according to claim 1, wherein the reactor is a fixed bed reactor.

3. The process according to claim 1, wherein the reactor is operated at a temperature of 150° C.-240° C.

4. The process according to claim 1, wherein the reactor is operated at a pressure of 20-80 atmospheres.

5. The process according to claim 1, further comprising hydrogenating the heated feed mixture in the reactor.

6. The process according to claim 5, wherein the hydrogenating is carried out by a supported catalyst in the fixed bed reactor.

7. The process according to claim 6, wherein the supported catalyst is a metal or metal oxide catalyst.

8. The process according to claim 7, wherein the supported catalyst comprises copper.

9. The process according to claim 1, further comprising mixing the condensed liquid with a glycerin feed.

10. The process according to claim 1, wherein the liquid phase stream is depressurized and cooled prior to distilling.

11. The process according to claim 1, wherein the liquid phase stream is distilled in multiple distillation columns.

* * * * *